(12) United States Patent
Amarasingham et al.

(10) Patent No.: US 9,536,052 B2
(45) Date of Patent: Jan. 3, 2017

(54) CLINICAL PREDICTIVE AND MONITORING SYSTEM AND METHOD

(75) Inventors: Rubendran Amarasingham, Dallas, TX (US); Timothy S. Swanson, Grapevine, TX (US); Christopher A. Clark, Dallas, TX (US); Yu Qian, Irving, TX (US); Sambamurthy Nalla, Flower Mound, TX (US); George R. Oliver, Southlake, TX (US); Kimberly P. Gerra, Keller, TX (US); Ying Ma, Southlake, TX (US)

(73) Assignee: Parkland Center for Clinical Innovation, Dallas, TX (US)

( * ) Notice: Subject to any disclaimer, the term of this patent is extended or adjusted under 35 U.S.C. 154(b) by 817 days.

(21) Appl. No.: 13/613,980

(22) Filed: Sep. 13, 2012

(65) Prior Publication Data

US 2013/0262357 A1 Oct. 3, 2013

Related U.S. Application Data

(60) Provisional application No. 61/552,525, filed on Oct. 28, 2011, provisional application No. 61/700,557, filed on Sep. 13, 2012.

(51) Int. Cl.
    *G06F 19/00* (2011.01)
(52) U.S. Cl.
    CPC ......... *G06F 19/345* (2013.01); *G06F 19/3431* (2013.01); *G06F 19/3443* (2013.01)
(58) Field of Classification Search
    None
    See application file for complete search history.

(56) References Cited

U.S. PATENT DOCUMENTS

| | | | |
|---|---|---|---|
| 7,395,216 B2 | 7/2008 | Rosenfeld | |
| 7,490,085 B2 | 2/2009 | Walker | |
| 8,595,159 B2 * | 11/2013 | McNair | A61B 5/021 706/12 |

(Continued)

OTHER PUBLICATIONS

Birge and Li. Using Fuzzy Neural Network to Solve Short-term Load Forecasting Problems. Dept of Industrial & Operations Engineering, University of Michigan. Technical Report 96-20. 1996.*

(Continued)

*Primary Examiner* — Stanley K Hill
*Assistant Examiner* — David H Kim
(74) *Attorney, Agent, or Firm* — Wei Wei Jeang; Grable Martin Fulton PLLC (57) ABSTRACT

A clinical predictive and monitoring system comprising a data store operable to receive and store data associated with a plurality of patients selected from medical and health data; and a number of social, behavioral, lifestyle, and economic data; at least one predictive model to identify at least one high-risk patient associated with at least one medical condition; a risk logic module operable to apply the at least one predictive model to the patient data to determine at least one risk score associated the at least one medical condition and identify at least one high-risk patient; a data presentation module operable to present notification and information to an intervention coordination team about the identified at least one high-risk patient; and an artificial intelligence tuning module adapted to automatically adjust parameters in the predictive model in response to trends in the patient data.

51 Claims, 5 Drawing Sheets

(56) References Cited

U.S. PATENT DOCUMENTS

| | | | |
|---|---|---|---|
| 2003/0101076 A1 | 5/2003 | Zaleski | |
| 2004/0122706 A1 | 6/2004 | Walker | |
| 2004/0122708 A1* | 6/2004 | Avinash et al. | 705/2 |
| 2004/0242972 A1 | 12/2004 | Adak | |
| 2005/0191716 A1 | 9/2005 | Surwit et al. | |
| 2005/0197982 A1* | 9/2005 | Saidi | G06N 3/02 706/21 |
| 2007/0094048 A1* | 4/2007 | Grichnik | 705/2 |
| 2008/0235049 A1 | 9/2008 | Morita | |
| 2008/0306763 A1* | 12/2008 | James | G06F 19/3418 705/2 |
| 2010/0017225 A1 | 1/2010 | Oakley et al. | |
| 2010/0083164 A1 | 4/2010 | Martin et al. | |
| 2010/0094648 A1 | 4/2010 | Seward | |
| 2010/0249531 A1 | 9/2010 | Hanlon et al. | |
| 2011/0009760 A1 | 1/2011 | Zhang | |
| 2011/0077973 A1 | 3/2011 | Breitenstein | |
| 2011/0202486 A1* | 8/2011 | Fung | G06N 7/005 706/12 |
| 2011/0225114 A1* | 9/2011 | Gotthardt | 706/50 |
| 2012/0084092 A1* | 4/2012 | Kozuch et al. | 705/2 |
| 2012/0101846 A1* | 4/2012 | Gotthardt et al. | 705/3 |
| 2014/0304200 A1* | 10/2014 | Wall | G06F 19/3418 706/12 |

OTHER PUBLICATIONS

Baxt, William G., et al. "A neural computational aid to the diagnosis of acute myocardial infarction." Annals of emergency medicine 39.4 (2002): 366-373.*

International Search Report and Written Opinion for PCT Appl. No. PCT/US2013/058159 dated Dec. 19, 2013 (9 pages).

Devan Kansagara, MD., MCR, et al, Risk Prediction Models for Hospital Readmission a Systematic Review, JAMA, Oct. 19, 2011—vol. 306, No. 15.

Ruben Amarasingham, MD, MBA, et al, An Automated Model to Identify Heart Failure Patients at Risk for 30-Day Readmission or Death Using Electronic Medical Record Data, www.lww-medicalcare.com, Medical Care, vol. 48, No. 11, Nov. 2010.

Alvarez, Carlos A., et al., "Predicting Out of Intensive Care Unit Cardiopulmonary Arrest or Death Using Electronic Medical Record Data," BMC Medical Informatics and Decision Making, Feb. 27, 2013, 11 pages.

Amarasingham, Ruben, et al., "Allocating Scarce Resources in Real-Time to Reduce Heart Failure Readmissions: A Prospective, Controlled Study," BMJ Quality and Safety Online First, Jul. 31, 2013, 10 pages.

Amarasingham, Ruben, et al., "An Automated Model to Identify Heart Failure Patients at Risk for 30-Day Readmission or Death Using Electronic Medical Record Data," Medical Care, vol. 48, No. 11, Nov. 2010, pp. 981-988.

Amarasingham, Ruben, et al., "Clinical Information Technology Capabilities in Four U.S. Hospitals, Testing a New Structural Performance Measure," Medical Care, vol. 44, No. 3, Mar. 2006, pp. 216-224.

Amarasingham, Ruben, et al., "Clinical Information Technologies and Inpatient Outcomes, a Multiple Hospital Study," Arch Intern Med, vol. 169, No. 2, Jan. 26, 2009, pp. 108-114.

Amarasingham, Ruben, et al., "Electronic Medical Record-Based Multicondition Models to Predict the Risk of 30 Day Readmission or Death Among Adult Medicine Patients: Validation and Comparison to Existing Models," BMC Medical Informatics and Decision Making, May 20, 2015, 8 pages.

Amarasingham, Ruben, et al., "Implementing Electronic Health Care Predictive Analytics: Considerations and Challengtes," Health Affairs, 33, No. 7, Jul. 2014, pp. 1148-1154.

Amarasingham, Ruben, et al., "A Rapid Admission Protocol to Reduce Emergency Department Boarding Times," BMJ Quality and Safety Online First, Feb. 8, 2010, pp. 200-204.

Bates, David W., et al., "Big Data in Health Care: Using Analytics to Identify and Manage High-Risk and High-Cost Patients," Health Affairs, 33, No. 7, Jul. 2014, pp. 1123-1131.

Bates, David W., "The Effects of Health Information Technology on Inpatient Care," Arch Intern Med, vol. 169, No. 2, Jan. 26, 2009, pp. 105-107.

Cohen, Glenn, et al., "The Legal and Ethical Concerns that Arise from Using Complex Predictive Analytics in Health Care,", Health Affairs, 33, No. 7, Jul. 2014, pp. 1139-1147.

Kansagara, Devan, et al., "Risk Prediction Models for Hospital Readmission, a Systematic Review," JAMA, vol. 306, No. 15, Oct. 19, 2011, pp. 1688-1698.

Makam, Anil N., et al., "Identifying Patients with Diabetes and the Earliest Data of Diagnosis in Real Time: An Electronic Health Record Case-Finding Algorithm," BMC Medical Informatics and Decision Making, Aug. 1, 2013, 7 pages.

McAlister, Finlay A., "Decreasing Readmissions: It Can Be Done But One Size Does Not Fit All," BMJ Quality and Safety Online First, Sep. 4, 2013, 3 pages.

Nehra, Mahendra S., et al., "Use of Administrative Claims Data for Identifying Patients with Cirrhosis," J Clin Gastroenterol, vol. 47, No. 5, May/Jun. 2013, pp. e50-e54.

Nijhawan, Ank E., "An Electronic Medical Record-Based Model to Predict 30-Day Risk of Readmission and Death Among HIV-Infected Inpatients," J Acquir Immune Defic Syndr, vol. 61, No. 3, Nov. 1, 2012, pp. 349-358.

Ram, Sudha, et al., "Predicting Asthma-Related Emergency Department Visits Using Big Data," IEEE Journal of Biomedical and Health Informatics, vol. 19, No. 4, Jul. 2015, pp. 1216-1223.

Singal, A.G., et al., "An Automated Model Using Electronic Medical Record Data Identifies Patients with Cirrhosis at High Risk for Readmission," Clinical Gastroenterology and Hepatology, vol. 11, No. 10, Oct. 2013, pp. 1335-1341.

* cited by examiner

CLINICAL PREDICTIVE AND MONITORING SYSTEM AND METHOD

RELATED APPLICATION

This patent application claims the benefit of U.S. Provisional Patent Application No. 61/552,525 entitled "Clinical Predictive and Monitoring System and Method" and filed on Oct. 28, 2011, and U.S. Provisional Application No. 61/700,557 entitled "Dashboard User Interface System and Method" filed on Sep. 13, 2012.

FIELD

The present disclosure relates to a clinical predictive and monitoring system and method.

BACKGROUND

The practice of medicine is increasingly characterized by overwhelming amounts of information, new knowledge in diagnostics and therapeutics, and highly fragmented care environments, with potentially hundreds of different individuals delivering care to a single patient across healthcare settings. Coordinating clinical decisions to advance the care and treatment of patients within this environment poses significant challenges. Hospital readmission is an important example of the type of problems health systems face in allocating critical resources in the midst of this fragmented environment.

Many patients are unnecessarily readmitted to the hospital. A 2009 study published in the *New England Journal of Medicine* (Jencks, S. F., et al., "Rehospitalizations among Patients in the Medicare Fee-for-Service Program," *The New England Journal of Medicine*, 360 (2009): 1418-28) demonstrated that almost one-fifth of Medicare patients were readmitted to the hospital within 30 days of discharge and 34% were readmitted within 90 days. This research estimated that only 10% of these readmissions were planned and that the annual cost to Medicare alone of unplanned hospital readmissions exceeds $17 billion.

For example, patients with heart failure, the leading diagnosis for acute care hospitalization and readmissions for patients over the age of 65, face particular challenges in transitioning from the hospital to home, and hospital readmissions are common for these patients. Preparation for discharge is often fragmented, and many patients and families feel ill-prepared for discharge. Upon discharge, responsibility for management of patients reverts back to their primary care provider, who may have no record of the care or medications given during the hospital stay. This lack of coordinated care results in frequent readmissions, with a large percentage of patients discharged with heart failure being readmitted to the hospital within several months.

While not all readmissions are preventable, it is estimated that a significant percentage of heart failure readmissions is avoidable with better patient education, better communication with the patient and the patient's primary care provider, ensuring that the patient has appropriate follow-up scheduled at the time of discharge, and other targeted intervention and treatment. However, most hospitals fail to consistently implement most or all of these elements. Many interventions can be expensive and complicated to perform in the real world. One of the reasons why efforts can fail is that hospitals have difficulty identifying patients that are truly at risk for readmission and for which interventions should be a high priority.

If high-risk patients could be more easily and accurately identified early in their hospital stay (e.g., in the Emergency Room or upon admission), the right interventions could be performed on the population for which it is most needed, thereby lowering overall heart failure readmission rates. Today, most hospitals attempting to identify patients at risk are doing so manually, without leveraging the information available in their electronic health records. Hospital readmission is one of potentially thousands of adverse clinical events that could be prevented by electronic identification, targeting, coordinating and monitoring throughout the inpatient and outpatient environment. This disclosure describes software developed to identify and risk stratify patients at highest risk for hospital readmissions and other adverse clinical events.

DETAILED DESCRIPTION

Figure 1:
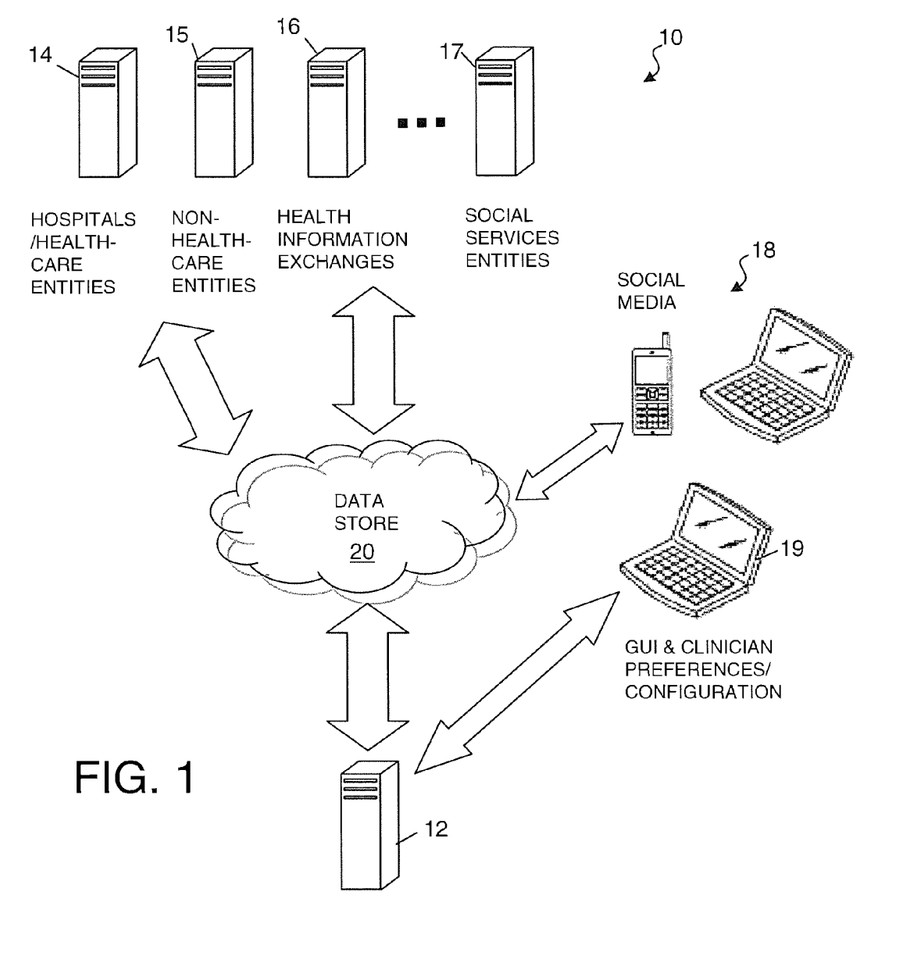
FIG. 1 is a simplified block diagram of an exemplary embodiment of a clinical predictive and monitoring system and method according to the present disclosure.

FIG. 1 is a simplified block diagram of an exemplary embodiment of a clinical predictive and monitoring system 10 according to the present disclosure. The clinical predictive and monitoring system 10 includes a computer system 12 adapted to receive a variety of clinical and non-clinical data relating to patients or individuals requiring care. The variety of data include real-time data streams and historical or stored data from hospitals and healthcare entities 14, non-health care entities 15, health information exchanges 16, and social-to-health information exchanges and social services entities 17, for example. These data are used to determine a disease risk score for selected patients so that they may receive more targeted intervention, treatment, and care that are better tailored and customized to their particular condition and needs. The system 10 is most suited for identifying particular patients who require intensive inpatient and/or outpatient care to avert serious detrimental effects of certain diseases and to reduce hospital readmission rates. It should be noted that the computer system 12 may comprise one or more local or remote computer servers operable to transmit data and communicate via wired and wireless communication links and computer networks.

The data received by the clinical predictive and monitoring system 10 may include electronic medical records (EMR) that include both clinical and non-clinical data. The EMR clinical data may be received from entities such as hospitals, clinics, pharmacies, laboratories, and health information exchanges, including: vital signs and other physiological data; data associated with comprehensive or focused history and physical exams by a physician, nurse, or allied health professional; medical history; prior allergy and adverse medical reactions; family medical history; prior surgical history; emergency room records; medication administration records; culture results; dictated clinical notes and records; gynecological and obstetric history; mental status examination; vaccination records; radiological imaging exams; invasive visualization procedures; psychiatric treatment history; prior histological specimens; laboratory data; genetic information; physician's notes; networked devices and monitors (such as blood pressure devices and glucose meters); pharmaceutical and supplement intake information; and focused genotype testing.

The EMR non-clinical data may include, for example, social, behavioral, lifestyle, and economic data; type and nature of employment; job history; medical insurance information; hospital utilization patterns; exercise information; addictive substance use; occupational chemical exposure; frequency of physician or health system contact; location and frequency of habitation changes; predictive screening health questionnaires such as the patient health questionnaire (PHQ); personality tests; census and demographic data; neighborhood environments; diet; gender; marital status; education; proximity and number of family or caregiving assistants; address; housing status; social media data; and educational level. The non-clinical patient data may further include data entered by the patients, such as data entered or uploaded to a social media website.

Additional sources or devices of EMR data may provide, for example, lab results, medication assignments and changes, EKG results, radiology notes, daily weight readings, and daily blood sugar testing results. These data sources may be from different areas of the hospital, clinics, patient care facilities, patient home monitoring devices, among other available clinical or healthcare sources.

As shown in FIG. 1, patient data sources may include non-healthcare entities 15. These are entities or organizations that are not thought of as traditional healthcare providers. These entities 15 may provide non-clinical data that include, for example, gender; marital status; education; community and religious organizational involvement; proximity and number of family or care-giving assistants; address; census tract location and census reported socioeconomic data for the tract; housing status; number of housing address changes; frequency of housing address changes; requirements for governmental living assistance; ability to make and keep medical appointments; independence to activities of daily living; hours of seeking medical assistance; location of seeking medical services; sensory impairments; cognitive impairments; mobility impairments; educational level; employment; and economic status in absolute and relative terms to the local and national distributions of income; climate data; and health registries. Such data sources may provide further insightful information about patient lifestyle, such as the number of family members, relationship status, individuals who might help care for a patient, and health and lifestyle preferences that could influence health outcomes.

The clinical predictive and monitoring system 10 may further receive data from health information exchanges (HIE) 16. HIEs are organizations that mobilize healthcare information electronically across organizations within a region, community or hospital system. HIEs are increasingly developed to share clinical and non-clinical patient data between healthcare entities within cities, states, regions, or within umbrella health systems. Data may arise from numerous sources such as hospitals, clinics, consumers, payers, physicians, labs, outpatient pharmacies, ambulatory centers, nursing homes, and state or public health agencies.

A subset of HIEs connect healthcare entities to community organizations that do not specifically provide health services, such as non-governmental charitable organizations, social service agencies, and city agencies. The clinical predictive and monitoring system 10 may receive data from these social services organizations and social-to-health information exchanges 17, which may include, for example, information on daily living skills, availability of transportation to doctor appointments, employment assistance, training, substance abuse rehabilitation, counseling or detoxification, rent and utilities assistance, homeless status and receipt of services, medical follow-up, mental health services, meals and nutrition, food pantry services, housing assistance, temporary shelter, home health visits, domestic violence, appointment adherence, discharge instructions, prescriptions, medication instructions, neighborhood status, and ability to track referrals and appointments.

Another source of data include social media or social network services 18, such as FACEBOOK and GOOGLE+ websites. Such sources can provide information such as the number of family members, relationship status, identify individuals who may help care for a patient, and health and lifestyle preferences that may influence health outcomes. These social media data may be received from the websites, with the individual's permission, and some data may come directly from a user's computing device as the user enters status updates, for example.

These non-clinical patient data provides a much more realistic and accurate depiction of the patient's overall holistic healthcare environment. Augmented with such non-clinical patient data, the analysis and predictive modeling performed by the present system to identify patients at high-risk of readmission or disease recurrence become much more robust and accurate.

The system 10 is further adapted to receive user preference and system configuration data from clinicians' computing devices (mobile devices, tablet computers, laptop computers, desktop computers, servers, etc.) 19 in a wired or wireless manner. These computing devices are equipped to display a system dashboard and/or another graphical user interface to present system data and reports. For example, a clinician (healthcare personnel) may immediately generate a list of patients that have the highest congestive heart failure risk scores, e.g., top n numbers or top x %. The graphical user interface are further adapted to receive the user's (healthcare personnel) input of preferences and configurations, etc. The data may be transmitted, presented, and displayed to the clinician/user in the form of web pages, web-based message, text files, video messages, multimedia messages, text messages, e-mail messages, and in a variety of suitable ways and formats.

As shown in FIG. 1, the clinical predictive and monitoring system 10 may receive data streamed real-time, or from historic or batched data from various data sources. Further, the system 10 may store the received data in a data store 20 or process the data without storing it first. The real-time and stored data may be in a wide variety of formats according to a variety of protocols, including CCD, XDS, HL7, SSO, HTTPS, EDI, CSV, etc. The data may be encrypted or otherwise secured in a suitable manner. The data may be pulled (polled) by the system 10 from the various data sources or the data may be pushed to the system 10 by the data sources. Alternatively or in addition, the data may be received in batch processing according to a predetermined schedule or on-demand. The data store 20 may include one or more local servers, memory, drives, and other suitable storage devices. Alternatively or in addition, the data may be stored in a data center in the cloud.

The computer system 12 may comprise a number of computing devices, including servers, that may be located locally or in a cloud computing farm. The data paths between the computer system 12 and the data store 20 may be encrypted or otherwise protected with security measures or transport protocols now known or later developed.

Figure 2:
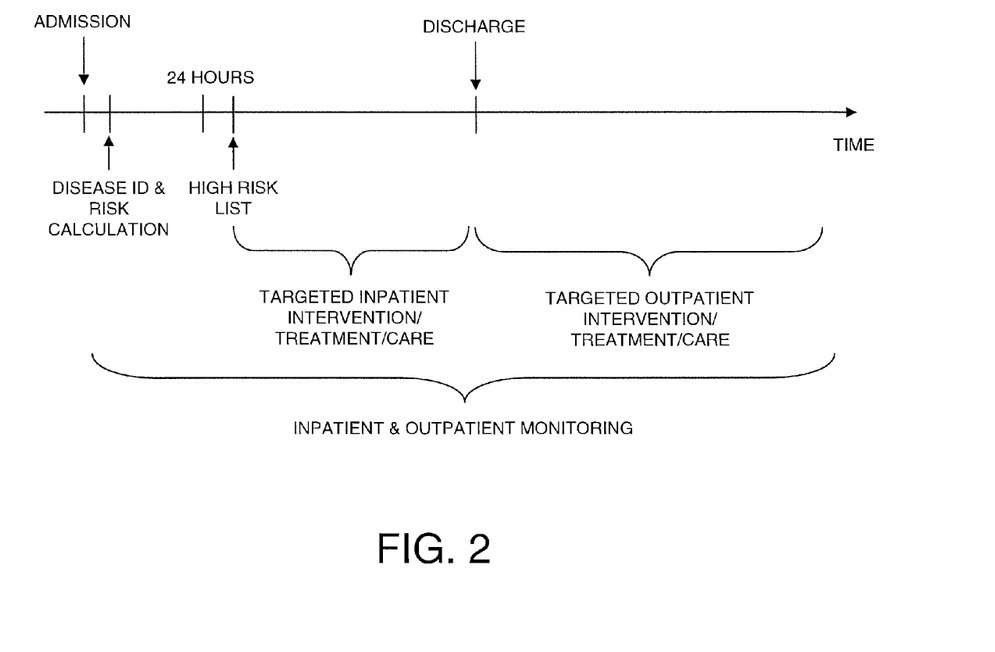
FIG. 2 is a timeline diagram of an exemplary embodiment of a clinical predictive and monitoring system and method according to the present disclosure.

FIG. 2 is a timeline diagram of an exemplary embodiment of a clinical predictive and monitoring system and method according to the present disclosure. The timeline diagram is used to illustrate how the clinical predictive and monitoring system and method 10 may be applied to reduce hospital readmission rate relating to congestive heart failure as an example. A majority of U.S. hospitals struggle to contain readmission rates related to congestive heart failure. Though numerous studies have found that some combination of careful discharge planning, care provider coordination, and intensive counseling can prevent subsequent rehospitalizations, success is difficult to achieve and sustain at the typical U.S. hospital. Enrolling all heart failure patients into a uniform, high intensity care transition program requires a depth of case management resources that is out of reach for many institutions, particularly safety-net hospitals. The clinical predictive and monitoring system and method 10 is adapted to accurately stratify risk for certain diseases and conditions such as 30-day readmission among congestive heart failure patients.

Within 24 hours of a patient's admission to the hospital, stored historical and real-time data related to the patients are analyzed by the clinical predictive and monitoring system and method 10 to identify specific diseases and conditions related to the patient, such as congestive heart failure. Further, the system 10 calculates a risk score for congestive heart failure for this particular patient within 24 hours of admission. If this particular patient's risk score for congestive heart failure is above a certain risk threshold, then the patient is identified on a list of high-risk patients that is presented to an intervention coordination team. The processes for disease identification and risk score calculation are described in more detail below.

The clinical predictive and monitoring system and method 10 are operable to display, transmit, and otherwise present the list of high risk patients to the intervention coordination team, which may include physicians, physician assistants, case managers, patient navigators, nurses, social workers, family members, and other personnel or individuals involved with the patient's care. The means of presentment may include e-mail, text messages, multimedia messages, voice messages, web pages, facsimile, audible or visual alerts, etc. delivered by a number of suitable electronic or portable computing devices. The intervention coordination team may then prioritize intervention for the highest risk patients and provide targeted inpatient care and treatment. The clinical predictive and monitoring system and method 10 may further automatically present a plan to include recommended intervention and treatment options. Some intervention plans may include detailed inpatient clinical assessment as well as patient nutrition, pharmacy, case manager, and heart failure education consults starting early in the patient's hospital stay. The intervention coordination team may immediately conduct the ordered inpatient clinical and social interventions. Additionally, the plan may include clinical and social outpatient interventions and developing a post-discharge plan of care and support.

High-risk patients are also assigned a set of high-intensity outpatient interventions. Once a targeted patient is discharged, outpatient intervention and care begin. Such interventions may include a follow-up phone call within 48 hours from the patient's case manager, such as a nurse; doctors' appointment reminders and medication updates; outpatient case management for 30 days; a follow-up appointment in a clinic within 7 days of discharge; a subsequent cardiology appointment if needed; and a follow-up primary care visit. Interventions that have been found to be successful are based on well-known readmission reduction programs and strategies designed to significantly reduce 30-day readmissions associated with congestive heart failure.

The clinical predictive and monitoring system and method 10 continue to receive clinical and non-clinical data regarding the patient identified as high risk during the hospital stay and after the patient's discharge from the hospital to further improve the diagnosis and modify or augment the treatment and intervention plan, if necessary.

After the patient is discharged from the hospital, the clinical predictive and monitoring system and method 10 continue to monitor patient intervention status according to the electronic medical records, case management systems, social services entities, and other data sources as described above. The clinical predictive and monitoring system and method 10 may also interact directly with caregivers, case managers, and patients to obtain additional information and to prompt action. For example, the clinical predictive and monitoring system and method 10 may notify a physician that one of his or her patients has returned to the hospital, the physician can then send a pre-formatted message to the system directing it to notify a specific case management team. In another example, the clinical predictive and monitoring system and method 10 may recognize that a patient missed a doctor's appointment and hasn't rescheduled. The system may send the patient a text message reminding the patient to reschedule the appointment.

Figure 3:
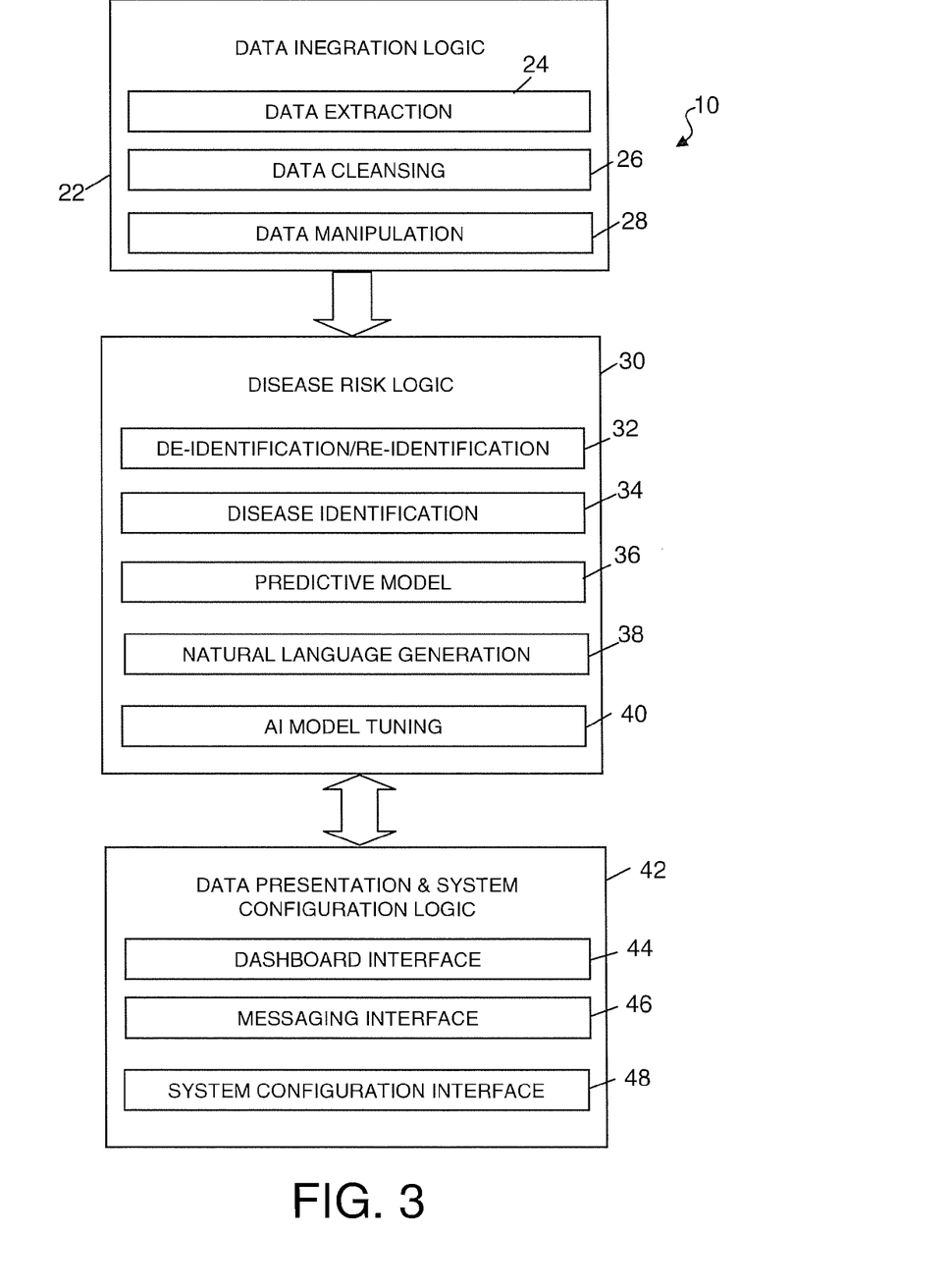
FIG. 3 is a simplified logical block diagram of an exemplary embodiment of a clinical predictive and monitoring system and method according to the present disclosure.

FIG. 3 is a simplified logical block diagram of an exemplary embodiment of a clinical predictive and monitoring system and method 10 according to the present disclosure. Because the system 10 receives and extracts data from many disparate sources in myriad formats pursuant to different protocols, the incoming data must first undergo a multi-step process before they may be properly analyzed and utilized. The clinical predictive and monitoring system and method 10 includes a data integration logic module 22 that further includes a data extraction process 24, a data cleansing process 26, and a data manipulation process 28. It should be noted that although the data integration logic module 22 is shown to have distinct processes 24-28, these are done for illustrative purposes only and these processes may be performed in parallel, iteratively, and interactively.

The data extraction process 24 extracts clinical and non-clinical data from data sources in real-time or in batches either directly or through the Internet, using various technologies and protocols. Preferably in real-time, the data cleansing process 26 "cleans" or pre-processes the data, putting structured data in a standardized format and preparing unstructured text for natural language processing (NLP) to be performed in the disease risk logic module 30 described below. The system may also receive "clean" data and convert them into desired formats (e.g., text date field converted to numeric for calculation purposes).

The data manipulation process 28 may analyze the representation of a particular data feed against a meta-data dictionary and determine if a particular data feed should be re-configured or replaced by alternative data feeds. For example, a given hospital EMR may store the concept of "maximum creatinine" in different ways. The data manipulation process 28 may make inferences in order to determine which particular data feed from the EMR would best represent the concept of "creatinine" as defined in the meta-data dictionary and whether a feed would need particular reconfiguration to arrive at the maximum value (e.g., select highest value).

The data integration logic module 22 then passes the pre-processed data to a disease risk logic module 30. The disease risk logic module 30 is operable to calculate a risk score associated with an identified disease or condition for each patient and identifying those patients who should receive targeted intervention and care. The disease risk logic module 30 includes a de-identification/re-identification process 32 that is adapted to remove all protected health information according to HIPAA standards before the data is transmitted over the Internet. It is also adapted to re-identify the data. Protected health information that may be removed and added back may include, for example, name, phone number, facsimile number, email address, social security number, medical record number, health plan beneficiary number, account number, certificate or license number, vehicle number, device number, URL, all geographical subdivisions smaller than a State, including street address, city, county, precinct, zip code, and their equivalent geocodes (except for the initial three digits of a zip code, if according to the current publicly available data from the Bureau of the Census), Internet Protocol number, biometric data, and any other unique identifying number, characteristic, or code.

The disease risk logic module 30 further includes a disease identification process 34. The disease identification process 34 is adapted to identify one or more diseases or conditions of interest for each patient. The disease identification process 34 considers data such as lab orders, lab values, clinical text and narrative notes, and other clinical and historical information to determine the probability that a patient has a particular disease. Additionally, during disease identification, natural language processing is conducted on unstructured clinical and non-clinical data to determine the disease or diseases that the physician believes are prevalent. This process 34 may be performed iteratively over the course of many days to establish a higher confidence in the disease identification as the physician becomes more confident in the diagnosis. The natural language processing combines a rule-based model and a statistically-based learning model.

The disease identification process 34 utilizes a hybrid model of natural language processing, which combines a rule-based model and a statistically-based learning model. During natural language processing, raw unstructured data, for example, physicians' notes and reports, first go through a process called tokenization. The tokenization process divides the text into basic units of information in the form of single words or short phrases by using defined separators such as punctuation marks, spaces, or capitalizations. Using the rule-based model, these basic units of information are identified in a meta-data dictionary and assessed according to predefined rules that determine meaning. Using the statistical-based learning model, the disease identification process 34 quantifies the relationship and frequency of word and phrase patterns and then processes them using statistical algorithms. Using machine learning, the statistical-based learning model develops inferences based on repeated patterns and relationships. The disease identification process 34 performs a number of complex natural language processing functions including text pre-processing, lexical analysis, syntactic parsing, semantic analysis, handling multi-word expression, word sense disambiguation, and other functions.

For example, if a physician's notes include the following: "55 yo m c h/o dm, cri. now with adib rvr, chfexac, and rle cellulitis going to 10 W, tele." The data integration logic 22 is operable to translate these notes as: "Fifty-five-year-old male with history of diabetes mellitus, chronic renal insufficiency now with atrial fibrillation with rapid ventricular response, congestive heart failure exacerbation and right lower extremity cellulitis going to 10 West and on continuous cardiac monitoring."

Continuing with the prior example, the disease identification process 34 is adapted to further ascertain the following: 1) the patient is being admitted specifically for atrial fibrillation and congestive heart failure; 2) the atrial fibrillation is severe because rapid ventricular rate is present; 3) the cellulitis is on the right lower extremity; 4) the patient is on continuous cardiac monitoring or telemetry; and 5) the patient appears to have diabetes and chronic renal insufficiency.

The disease risk logic module 30 further comprises a predictive model process 36 that is adapted to predict the risk of particular diseases or condition of interest according to one or more predictive models. For example, if the hospital desires to determine the level of risk for future heart failure readmission for all patients currently admitted with heart failure, the heart failure predictive model may be selected for processing patient data. However, if the hospital desires to determine the risk levels for all internal medicine patients for any cause, an all-cause readmissions predictive model may be used to process the patient data. As another example, if the hospital desires to identify those patients at risk for short-term and long-term diabetic complications, the diabetes predictive model may be used to target those patients. Other predictive models may include HIV readmission, diabetes identification, risk for cardio-pulmonary arrest, kidney disease progression, acute coronary syndrome, pneumonia, cirrhosis, all-cause disease-independent readmission, colon cancer pathway adherence, and others.

Continuing to use the prior example, the predictive model for congestive heart failure may take into account a set of risk factors or variables, including the worst values for laboratory and vital sign variables such as: albumin, total bilirubin, creatine kinase, creatinine, sodium, blood urea nitrogen, partial pressure of carbon dioxide, white blood cell count, troponin-I, glucose, internationalized normalized ratio, brain natriuretic peptide, pH, temperature, pulse, diastolic blood pressure, and systolic blood pressure. Further, non-clinical factors are also considered, for example, the number of home address changes in the prior year, risky health behaviors (e.g., use of illicit drugs or substance), number of emergency room visits in the prior year, history of depression or anxiety, and other factors. The predictive model specifies how to categorize and weight each variable or risk factor, and the method of calculating the predicted probably of readmission or risk score. In this manner, the clinical predictive and monitoring system and method 10 is able to stratify, in real-time, the risk of each patient that arrives at a hospital or another healthcare facility. Therefore, those patients at the highest risks are automatically identified so that targeted intervention and care may be instituted. One output from the disease risk logic module 30 includes the risk scores of all the patients for particular disease or condition. In addition, the module 30 may rank the patients according to the risk scores, and provide the identities of those patients at the top of the list. For example, the hospital may desire to identify the top 20 patients most at risk for congestive heart failure readmission, and the top 5% of patients most at risk for cardio-pulmonary arrest in the next 24 hours. Other diseases and conditions that may be identified using predictive modeling include, for example, HIV readmission, diabetes identification, kidney disease progression, colorectal cancer continuum screening, meningitis management, acid-base management, anticoagulation management, etc.

The disease risk logic module 30 may further include a natural language generation module 38. The natural language generation module 38 is adapted to receive the output from the predictive model 36 such as the risk score and risk variables for a patient, and "translate" the data to present the evidence that the patient is at high-risk for that disease or condition. This module 30 thus provides the intervention coordination team additional information that supports why the patient has been identified as high-risk for the particular disease or condition. In this manner, the intervention coordination team may better formulate the targeted inpatient and outpatient intervention and treatment plan to address the patient's specific situation.

The disease risk logic module 30 further includes an artificial intelligence (AI) model tuning process 40. The artificial intelligence model tuning process 38 utilizes adaptive self-learning capabilities using machine learning technologies. The capacity for self-reconfiguration enables the system and method 10 to be sufficiently flexible and adaptable to detect and incorporate trends or differences in the underlying patient data or population that may affect the predictive accuracy of a given algorithm. The artificial intelligence model tuning process 40 may periodically retrain a selected predictive model for improved accurate outcome to allow for selection of the most accurate statistical methodology, variable count, variable selection, interaction terms, weights, and intercept for a local health system or clinic. The artificial intelligence model tuning process 40 may automatically modify or improve a predictive model in three exemplary ways. First, it may adjust the predictive weights of clinical and non-clinical variables without human supervision. Second, it may adjust the threshold values of specific variables without human supervision. Third, the artificial intelligence model tuning process 40 may, without human supervision, evaluate new variables present in the data feed but not used in the predictive model, which may result in improved accuracy. The artificial intelligence model tuning process 40 may compare the actual observed outcome of the event to the predicted outcome then separately analyze the variables within the model that contributed to the incorrect outcome. It may then re-weigh the variables that contributed to this incorrect outcome, so that in the next reiteration those variables are less likely to contribute to a false prediction. In this manner, the artificial intelligence model tuning process 40 is adapted to reconfigure or adjust the predictive model based on the specific clinical setting or population in which it is applied. Further, no manual reconfiguration or modification of the predictive model is necessary. The artificial intelligence model tuning process 40 may also be useful to scale the predictive model to different health systems, populations, and geographical areas in a rapid timeframe.

As an example of how the artificial intelligence model tuning process 40 functions, the sodium variable coefficients may be periodically reassessed to determine or recognize that the relative weight of an abnormal sodium laboratory result on a new population should be changed from 0.1 to 0.12. Over time, the artificial intelligence model tuning process 38 examines whether thresholds for sodium should be updated. It may determine that in order for the threshold level for an abnormal sodium laboratory result to be predictive for readmission, it should be changed from, for example, 140 to 136 mg/dL. Finally, the artificial intelligence model tuning process 40 is adapted to examine whether the predictor set (the list of variables and variable interactions) should be updated to reflect a change in patient population and clinical practice. For example, the sodium variable may be replaced by the NT-por-BNP protein variable, which was not previously considered by the predictive model.

The results from the disease risk logic module 30 are provided to the hospital personnel, such as the intervention coordination team, and other caretakers by a data presentation and system configuration logic module 42. The data presentation logic module 42 includes a dashboard interface 44 that is adapted to provide information on the performance of the clinical predictive and monitoring system and method 10. A user (e.g., hospital personnel, administrator, and intervention coordination team) is able to find specific data they seek through simple and clear visual navigation cues, icons, windows, and devices. The interface may further be responsive to audible commands, for example. Because the number of patients a hospital admits each day can be overwhelming, a simple graphical interface that maximizes efficiency and reduce user navigation time is desirable. The visual cues are preferably presented in the context of the problem being evaluated (e.g., readmissions, out-of-ICU, cardiac arrest, diabetic complications, among others).

The dashboard user interface 44 allows interactive requesting of a variety of views, reports and presentations of extracted data and risk score calculations from an operation database within the system. Including, for example, summary views of a list of patient in a specific care location; detailed explanation of the components of the various sub-scores; graphical representations of the data for a patient or population over time; comparison of incidence rates of predicted events to the rates of prediction in a specified time frame; summary text clippings, lab trends and risk scores on a particular patient for assistance in dictation or preparation of history and physical reports, daily notes, sign-off continuity of care notes, operative notes, discharge summaries, continuity of care documents to outpatient medical practitioners; order generation to automate the generation of orders authorized by a local care providers healthcare environment and state and national guidelines to be returned to the practitioner's office, outside healthcare provider networks or for return to a hospital or practices electronic medical record; aggregation of the data into frequently used medical formulas to assist in care provision including but not limited to: acid-base calculation, MELD score, Child-Pugh-Turcot score, TIMI risk score, CHADS score, estimated creatinine clearance, Body Surface area, Body Mass Index, adjuvant, neoadjuvant and metastatic cancer survival nomograms, MEWS score, APACHE score, SWIFT score, NIH stroke scale, PORT score, AJCC staging; and publishing of elements of the data on scanned or electronic versions of forms to create automated data forms.

The data presentation and system configuration logic module 40 further includes a messaging interface 46 that is adapted to generate output messaging code in forms such as HL7 messaging, text messaging, e-mail messaging, multimedia messaging, web pages, web portals, REST, XML, computer generated speech, constructed document forms containing graphical, numeric, and text summary of the risk assessment, reminders, and recommended actions. The interventions generated or recommended by the system and method 10 may include: risk score report to the primary physician to highlight risk of readmission for their patients; score report via new data field input into the EMR for use by population surveillance of entire population in hospital, covered entity, accountable care population, or other level of organization within a healthcare providing network; comparison of aggregate risk of readmissions for a single hospital or among hospitals to allow risk-standardized comparisons of hospital readmission rates; automated incorporation of score into discharge summary template, continuity of care document (within providers in the inpatient setting or to outside physician consultants and primary care physicians), HL7 message to facility communication of readmission risk transition to nonhospital physicians; and communicate subcomponents of the aggregate social-environmental score, clinical score and global risk score. These scores would highlight potential strategies to reduce readmissions including: generating optimized medication lists; allowing pharmacies to identify those medication on formulary to reduce out-of-pocket cost and improve outpatient compliance with the pharmacy treatment plan; flagging nutritional education needs; identifying transportation needs; assessing housing instability to identify need for nursing home placement, transitional housing, Section 8 HHS housing assistance; identifying poor self regulatory behavior for additional follow-up phone calls; identifying poor social network scores leading to recommendation for additional in home RN assessment; flagging high substance abuse score for consultation of rehabilitation counseling for patients with substance abuse issues.

This output may be transmitted wirelessly or via LAN, WAN, the Internet, and delivered to healthcare facilities' electronic medical record stores, user electronic devices (e.g., pager, text messaging program, mobile telephone, tablet computer, mobile computer, laptop computer, desktop computer, and server), health information exchanges, and other data stores, databases, devices, and users. The system and method 10 may automatically generate, transmit, and present information such as high-risk patient lists with risk scores, natural language generated text, reports, recommended actions, alerts, Continuity of Care Documents, flags, appointment reminders, and questionnaires.

The data presentation and system configuration logic module 40 further includes a system configuration interface 48. Local clinical preferences, knowledge, and approaches may be directly provided as input to the predictive models through the system configuration interface 46. This system configuration interface 46 allows the institution or health system to set or reset variable thresholds, predictive weights, and other parameters in the predictive model directly. The system configuration interface 48 preferably includes a graphical user interface designed to minimize user navigation time.

Figure 4:
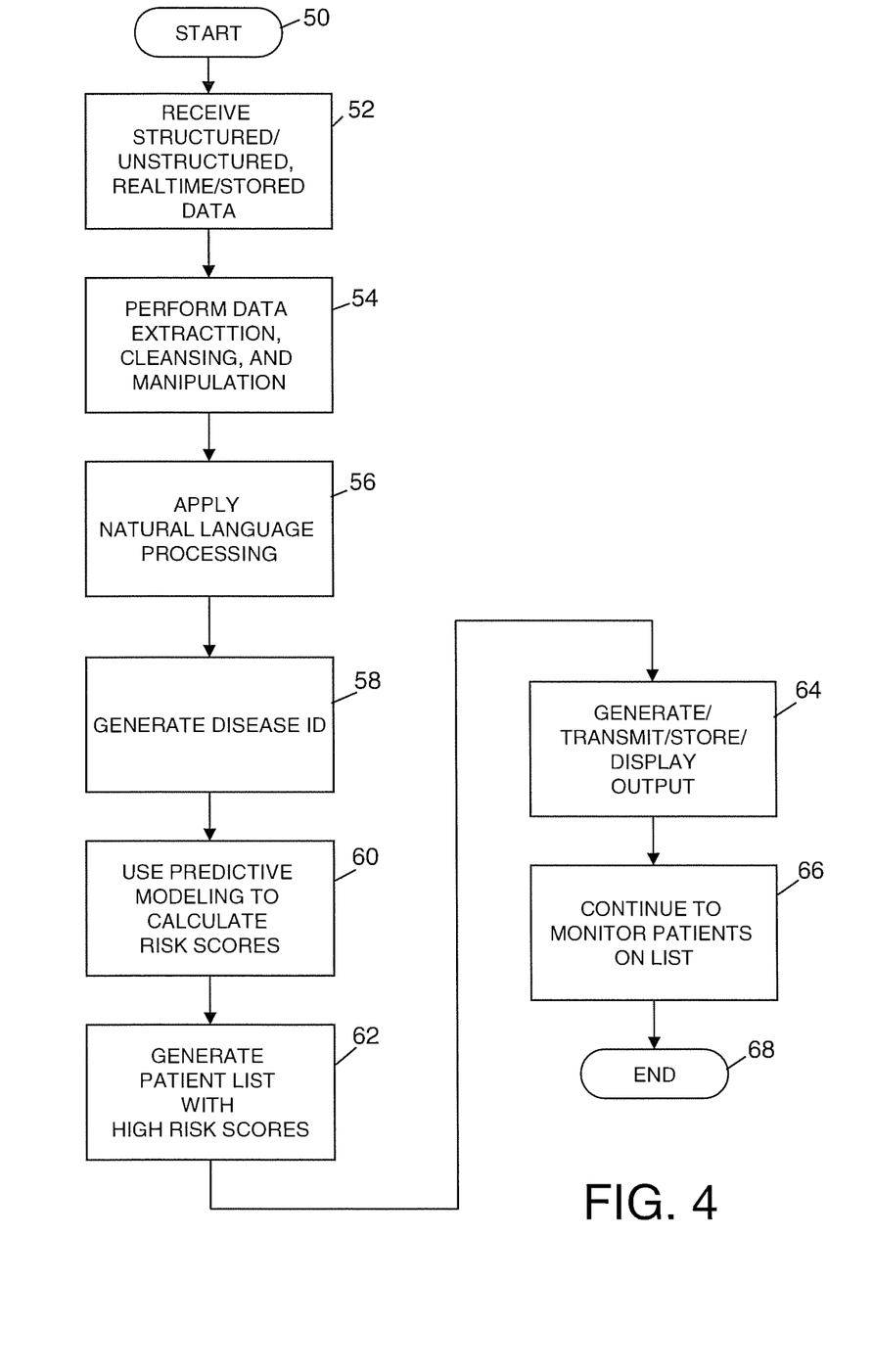
FIG. 4 is a simplified flowchart of an exemplary embodiment of a clinical predictive and monitoring method according to the present disclosure.

FIG. 4 is a simplified flowchart of an exemplary embodiment of a clinical predictive and monitoring method 50 according to the present disclosure. The method 50 receives structured and unstructured clinical and non-clinical data related to specific patients from a variety of sources and in a number of different formats, as shown in block 52. These data may be encrypted or protected using data security methods now known or later developed. In block 54, the method 50 pre-processes the received data, such as data extraction, data cleansing, and data manipulation. Other data processing techniques now known and later developed may be utilized. In block 56, data processing methods such as natural language processing and other suitable techniques may be used to translate or otherwise make sense of the data. In block 58, by analyzing the pre-processed data, one or more diseases or conditions of interest as related to each patient are identified. In block 60, the method 50 applies one or more predictive models to further analyze the data and calculate one or more risk scores for each patient as related to the identified diseases or conditions. In blocks 62 and 64, one or more lists showing those patients with the highest risks for each identified disease or condition are generated, transmitted, and otherwise presented to hospital personnel, such as members of an intervention coordination team. These lists may be generated on a daily basis or according to another desired schedule. The intervention coordination team may then prescribe and follow targeted intervention and treatment plans for inpatient and outpatient care. In block 66, those patients identified as high-risk are continually monitored while they are undergoing inpatient and outpatient care. The method 50 ends in block 68.

Not shown explicitly in FIG. 4 is the de-identification process, in which the data become disassociated with the patient's identity to comply with HIPAA regulations. The data can be de-coupled with the patient's identity whenever they are transmitted over wired or wireless network links that may be compromised, and otherwise required by HIPAA. The method 50 is further adapted to reunite the patient data with the patient's identity.

Figure 5:
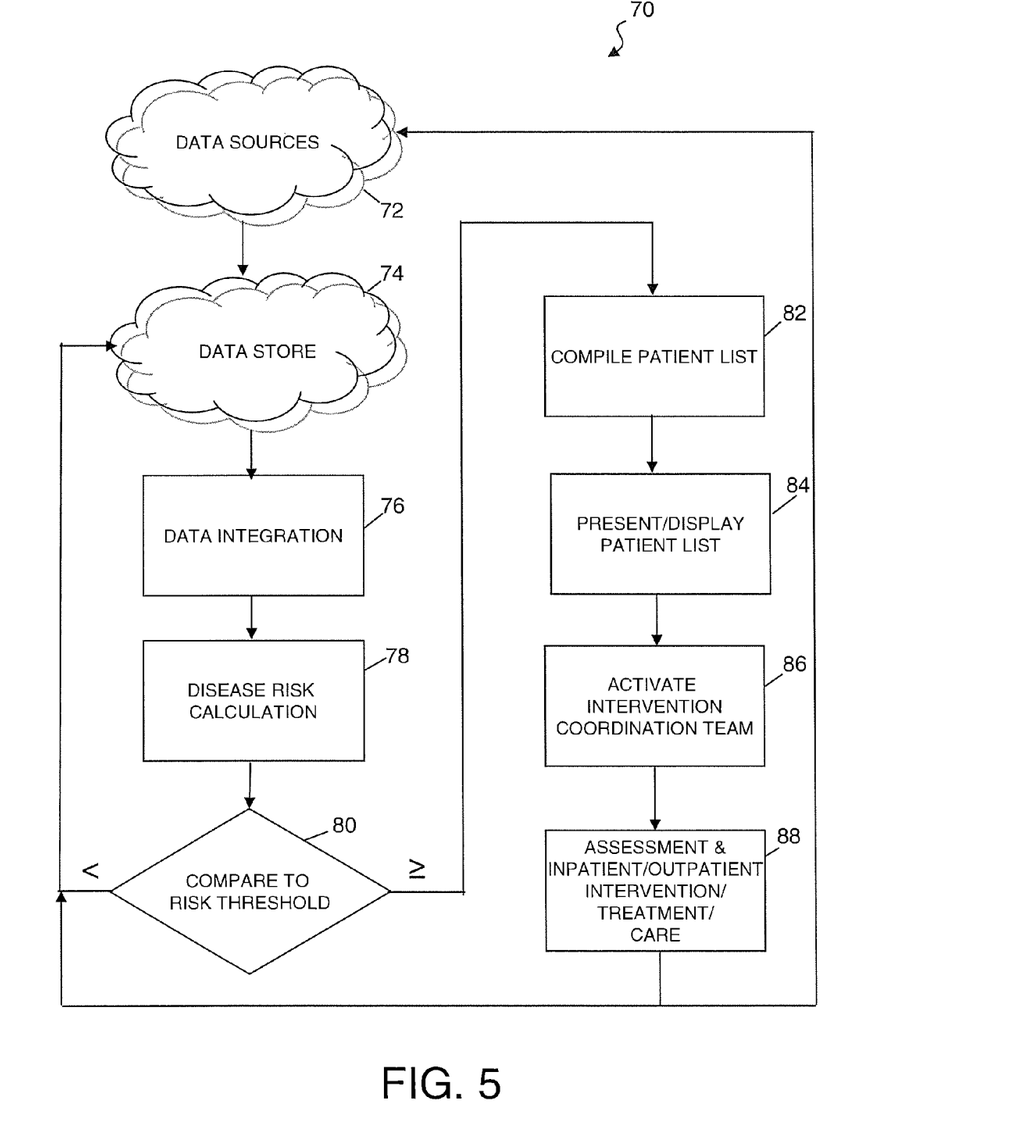
FIG. 5 is a simplified flowchart/block diagram of an exemplary embodiment of a clinical predictive and monitoring method according to the present disclosure.

FIG. 5 is a simplified flowchart/block diagram of an exemplary embodiment of a clinical predictive and monitoring method 70 according to the present disclosure. A variety of data are received from a number of disparate data sources 72 related to particular patients admitted at a hospital or a healthcare facility. The incoming data may be received in real-time or the data may be stored as historical data received in batches or on-demand. The incoming data are stored in a data store 74. In block 76, the received data undergo a data integration process (data extraction, data cleansing, data manipulation), as described above. The resultant pre-processed data then undergoes the disease logic process 78 during which de-identification, disease identification, and predictive modeling are performed. The risk score computed for each patient for a disease of interest is compared to a disease risk threshold in block 80. Each disease is associated with its own risk threshold. If the risk score is less than the risk threshold, then the process returns to data integration and is repeated when new data associated with a patient become available. If the risk score is greater than or equal to the risk threshold, then the identified patient having the high risk score is included in a patient list in block 82. In block 84, the patient list and other associated information may then be presented to the intervention coordination team in one or more possible ways, such as transmission to and display on a mobile device in the form of a text message, e-mail message, web page, etc. In this manner, an intervention coordination team is notified and activated to target the patients identified in the patient list for assessment, and inpatient and outpatient treatment and care, as shown in block 88. The process may thereafter provide feedback data to the data sources 72 and/or return to data integration 76 that continues to monitor the patient during his/her targeted inpatient and outpatient intervention and treatment. Data related to the patient generated during the inpatient and outpatient care, such as prescribed medicines and further laboratory results, radiological images, etc. is continually monitored according to pre-specified algorithms which define the patient's care plan.

The system as described herein is operable to harness, simplify and sort patient information in real-time, predict and identify highest risk patients, coordinate and alert practitioners, and monitor patient outcomes across time and space. The present system improves healthcare efficiency and assists with resource allocation that leads to better patient outcomes.

The features of the present invention which are believed to be novel are set forth below with particularity in the appended claims. However, modifications, variations, and changes to the exemplary embodiments described above will be apparent to those skilled in the art, and the clinical predictive and monitoring system and method described herein thus encompasses such modifications, variations, and changes and are not limited to the specific embodiments described herein.

What is claimed is:

1. A clinical predictive and monitoring system, comprising:
    a data store configured to receive and store data associated with a plurality of patients including clinical and non-clinical data;
    at least one predictive model including a plurality of weighted risk variables and risk thresholds in consideration of the clinical and non-clinical data to identify at least one high-risk patient as having a high risk of developing at least one specified medical condition;
    a risk logic module configured to apply the at least one predictive model to the patient clinical and non-clinical data of the plurality of patients to determine at least one risk score associated with the at least one specified medical condition for each patient, and identify at least one high-risk patient from among the plurality of patients as having a high risk of developing the at least one specified medical condition indicated by the risk scores; and
    a data presentation module configured to present notification and information to an intervention coordination team about the identified at least one high-risk patient.

2. The system of claim 1, further comprising an artificial intelligence tuning module configured to automatically adjust the weights of the plurality of risk variables in response to trends in patient data.

3. The system of claim 1, further comprising an artificial intelligence tuning module configured to automatically adjust the risk thresholds of the plurality of risk variables in response to trends in patient data.

4. The system of claim 1, further comprising an artificial intelligence tuning module configured to automatically add or remove risk variables in the at least one predictive model in response to trends in patient data.

5. The system of claim 1, further comprising an artificial intelligence tuning module configured to automatically adjust at least one of the weights, risk thresholds, and risk variables in response to trends in patient data.

6. The system of claim 1, further comprising an artificial intelligence tuning module configured to automatically adjust a parameter in the predictive model in response to detecting a change in the overall patient data to improve the accuracy of risk score determination.

7. The system of claim 1, wherein the data store is configured to receive and store real-time and historic data.

8. The system of claim 1, wherein the data presentation module is further configured to generate and transmit notification and information in a form selected from at least one member of the group consisting of text message, multimedia message, instant message, voice message, e-mail message, web page, web-based message, web pages, web-based message, and text files.

9. The system of claim 1, wherein the data presentation module is further configured to generate and transmit notification and information to at least one mobile device.

10. The system of claim 1, wherein the data presentation module further comprises a dashboard interface configured to present and display information in response to a user request.

11. The system of claim 1, further comprising a system configuration interface configured to receive configuration data from a user to initiate or adjust system operations.

12. The system of claim 1, further comprising a system configuration interface configured to set or reset at least one of the risk variable thresholds and weights in the predictive model.

13. The system of claim 1, wherein the risk logic module is further configured to analyze the clinical and non-clinical data and identify a disease associated with at least one of the plurality of patients.

14. The system of claim 1, wherein the data store is further configured to continue receiving and storing clinical and non-clinical data generated after a patient's admission to a hospital, and the risk logic module is operable to continue applying at least one predictive model associated with an identified disease to a data set including all clinical and non-clinical data associated with the patient.

15. The system of claim 1, wherein the data store is further configured to continue receiving and storing clinical and non-clinical data generated after a patient's discharge from a hospital, and the risk logic module is operable to continue applying at least one predictive model associated with an identified disease to a data set including all clinical and non-clinical data associated with the patient.

16. The system of claim 1, further comprising a data integration logic module configured to receive the clinical and non-clinical patient data, and perform data extraction, data cleansing, and data manipulation on the received data.

17. The system of claim 1, further comprising a data integration logic module configured to receive the clinical and non-clinical patient data, and perform natural language processing.

18. The system of claim 17, wherein the data integration logic module is configured to apply a plurality of rules and a statistical model to the patient data.

19. The system of claim 17, further comprising a data integration logic module including a rule-based model and a statistically-based learning model.

20. The system of claim 19, wherein the statistical-based learning model is configured to develop inferences based on repeated patterns and relationships in the patient data.

21. The system of claim 17, wherein the data integration logic module is configured to analyze the received and stored patient data, identify data elements, and map those data elements to definitions in a data dictionary.

22. The system of claim 1, wherein the data store is configured to receive and store data extracted from social media websites.

23. A clinical predictive and monitoring system, comprising:
    a data store configured to receive and store data associated with a plurality of patients including clinical and non-clinical data;
    at least one predictive model for at least one specified medical condition configured to process the patient clinical and non-clinical data to identify at least one high-risk patient as having a high risk of developing the at least one specified medical condition;

a risk logic module configured to apply the at least one predictive model to the patient clinical and non-clinical data of the plurality of patients to determine at least one risk score associated with the at least one specified medical condition for each patient, and identify at least one high-risk patient for the at least one specified medical condition indicated by the risk scores;

a data presentation module configured to present notification and information to an intervention coordination team about the identified at least one high-risk patient; and an artificial intelligence tuning module configured to automatically adjust parameters in the predictive model in response to trends in the patient data.

24. The system of claim 23, wherein the artificial intelligence tuning module is further configured to automatically adjust the risk thresholds of the plurality of risk variables in response to trends in patient data.

25. The system of claim 23, wherein the artificial intelligence tuning module is further configured to automatically add or remove risk variables in the at least one predictive model in response to trends in patient data.

26. The system of claim 23, wherein the artificial intelligence tuning module is further configured to automatically adjust at least one of the weights, risk thresholds, and risk variables in response to trends in patient data.

27. The system of claim 23, wherein the data store is configured to receive and store real-time and historic data.

28. The system of claim 23, wherein the data presentation module is further configured to generate and transmit notification and information in a form selected from at least one member of the group consisting of text message, multimedia message, instant message, voice message, e-mail message, web page, web-based message, web pages, web-based message, and text files.

29. The system of claim 23, wherein the data presentation module is further configured to generate and transmit notification and information to at least one mobile device.

30. The system of claim 23, wherein the data presentation module further comprises a dashboard interface configured to present and display information in response to a user request.

31. The system of claim 23, further comprising a system configuration interface configured to receive configuration data from a user to initiate or adjust system operations.

32. The system of claim 23, further comprising a system configuration interface configured to set or reset at least one of the risk variable thresholds and weights in the predictive model.

33. The system of claim 23, wherein the risk logic module is further configured to analyze the clinical and non-clinical data and identify a disease associated with at least one of the plurality of patients.

34. The system of claim 23, wherein the data store is further configured to continue receiving and storing clinical and non-clinical data generated after a patient's admission to a hospital, and the risk logic module is configured to continue applying at least one predictive model associated with an identified disease to a data set including all clinical and non-clinical data associated with the patient.

35. The system of claim 23, wherein the data store is further configured to continue receiving and storing clinical and non-clinical data generated after a patient's discharge from a hospital, and the risk logic module is configured to continue applying at least one predictive model associated with an identified disease to a data set including all clinical and non-clinical data associated with the patient.

36. The system of claim 23, further comprising a data integration logic module configured to receive the clinical and non-clinical patient data, and perform data extraction, data cleansing, and data manipulation on the received data.

37. The system of claim 23, further comprising a data integration logic module configured to receive the clinical and non-clinical patient data, and perform natural language processing.

38. The system of claim 37, wherein the data integration logic module is configured to apply a plurality of rules and a statistical model to the patient data.

39. The system of claim 37, further comprising a data integration logic module including a rule-based model and a statistically-based learning model.

40. The system of claim 39, wherein the statistical-based learning model is configured to develop inferences based on repeated patterns and relationships in the patient data.

41. A computerized method of providing clinical screening, diagnosis, treatment, monitoring and palliation, comprising:

receiving and storing data associated with a plurality of patients including clinical and non-clinical data;

processing the clinical and non-clinical data of the plurality of patients with a predictive model configured with risk variables and risk thresholds of at least one specified medical condition;

computing, using the predictive model, a risk score in response to the risk variables and risk thresholds for each patient that is indicative of the patient's risk for developing the at least one specified medical condition;

in response to the computed risk scores, identifying at least one high-risk patient as having a high risk of developing the at least one specified medical condition;

presenting at least one of visual and audible notification to an intervention coordination team about the identified at least one high-risk patient; and automatically monitoring and adjusting parameters in the predictive model in response to trends in the patient clinical and non-clinical data.

42. The method of claim 41, wherein receiving and storing data comprises receiving and storing patient data from data sources selected from at least one member of the group consisting of: hospitals, clinics, health information exchanges, pharmacies, laboratories, social services entities, and social media websites.

43. The system of claim 23, wherein the risk logic module is further adapted to generate evidence supporting the identification of the patient as high-risk.

44. The system of claim 1 or 23, wherein the clinical data are selected from at least one member of the group consisting of: vital signs and other physiological data; data associated with physical exams by a physician, nurse, or allied health professional; medical history; allergy and adverse medical reactions; family medical information; prior surgical information; emergency room records; medication administration records; culture results; dictated clinical notes and records; gynecological and obstetric information; mental status examination; vaccination records; radiological imaging exams; invasive visualization procedures; psychiatric treatment information; prior histological specimens; laboratory data; genetic information; physician's and nurses' notes; networked devices and monitors; pharmaceutical and supplement intake information; and focused genotype testing.

45. The system of claim 1 or 23, wherein the clinical data comprises: vital signs; data associated with physical exams by a physician, nurse, or allied health professional; medical history; allergy and adverse medical reactions; family medical information; prior surgical information; emergency room records; medication administration records; culture results; dictated clinical notes and records; vaccination records; radiological imaging exams; laboratory data; genetic information; physician's and nurses' notes; pharmaceutical and supplement intake information; and focused genotype testing.

46. The system of claim 1 or 23, wherein the non-clinical data are selected from at least one member of the group consisting of: social, behavioral, lifestyle, and economic data; type and nature of employment data; job history data; medical insurance information; hospital utilization patterns; exercise information; addictive substance use data; occupational chemical exposure records; frequency of physician or health system contact logs; location and frequency of habitation change data; predictive screening health questionnaires; personality tests; census and demographic data; neighborhood environment data; dietary data; participation in food, housing, and utilities assistance registries; gender; marital status; education data; proximity and number of family or care-giving assistant data; address data; housing status data; social media data; educational level data; and data entered by patients.

47. The system of claim 1 or 23, wherein the non-clinical data comprises: social, behavioral, lifestyle, and economic data; type and nature of employment data; job history data; medical insurance information; hospital utilization patterns; exercise information; substance use data; occupational chemical exposure records; frequency of physician or health system contact logs; location and frequency of habitation change data; census and demographic data; neighborhood environment data; dietary data; participation in food, housing, and utilities assistance registries; gender; marital status; education data; proximity and number of family or care-giving assistant data; address data; housing status data; social media data; educational level data; and data entered by patients.

48. The method of claim 41, wherein receiving clinical data comprise receiving clinical data selected from at least one member of the group consisting of: vital signs and other physiological data; data associated with physical exams by a physician, nurse, or allied health professional; medical history; allergy and adverse medical reactions; family medical information; prior surgical information; emergency room records; medication administration records; culture results; dictated clinical notes and records; gynecological and obstetric information; mental status examination; vaccination records; radiological imaging exams; invasive visualization procedures; psychiatric treatment information; prior histological specimens; laboratory data; genetic information; physician's and nurses' notes; networked devices and monitors; pharmaceutical and supplement intake information; and focused genotype testing.

49. The method of claim 41, wherein receiving clinical data comprise receiving: vital signs; data associated with physical exams by a physician, nurse, or allied health professional; medical history; allergy and adverse medical reactions; family medical information; prior surgical information; emergency room records; medication administration records; culture results; dictated clinical notes and records; vaccination records; radiological imaging exams; laboratory data; genetic information; physician's and nurses' notes; pharmaceutical and supplement intake information; and focused genotype testing.

50. The method of claim 41, wherein receiving clinical data comprise receiving non-clinical data at least one member of the group consisting of: social, behavioral, lifestyle, and economic data; type and nature of employment data; job history data; medical insurance information; hospital utilization patterns; exercise information; addictive substance use data; occupational chemical exposure records; frequency of physician or health system contact logs; location and frequency of habitation change data; predictive screening health questionnaires; personality tests; census and demographic data; neighborhood environment data; dietary data; participation in food, housing, and utilities assistance registries; gender; marital status; education data; proximity and number of family or care-giving assistant data; address data; housing status data; social media data; educational level data; and data entered by patients.

51. The method of claim 41, wherein receiving non-clinical data comprise receiving: social, behavioral, lifestyle, and economic data; type and nature of employment data; job history data; medical insurance information; hospital utilization patterns; exercise information; substance use data; occupational chemical exposure records; frequency of physician or health system contact logs; location and frequency of habitation change data; census and demographic data; neighborhood environment data; dietary data; participation in food, housing, and utilities assistance registries; gender; marital status; education data; proximity and number of family or care-giving assistant data; address data; housing status data; social media data; educational level data; and data entered by patients.

* * * * *